(12) United States Patent
Dottori et al.

(10) Patent No.: US 7,851,142 B2
(45) Date of Patent: *Dec. 14, 2010

(54) METHOD OF REDUCING GLYCOLYSIS IN PLATELET CONCENTRATES USING L-CARNITINE, ALKANOYL CARNITINES AND SALTS THEREOF

(75) Inventors: Secondo Dottori, Rome (IT); Arduino Arduini, Pescara (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 734 days.

This patent is subject to a terminal disclaimer.

(21) Appl. No.: 11/770,136

(22) Filed: Jun. 28, 2007

(65) Prior Publication Data

US 2007/0248941 A1  Oct. 25, 2007

Related U.S. Application Data

(60) Division of application No. 10/756,368, filed on Jan. 14, 2004, which is a continuation of application No. 10/055,900, filed on Jan. 28, 2002, now abandoned, which is a continuation of application No. 09/327,465, filed on Jun. 8, 1999, now Pat. No. 6,403,124, which is a continuation-in-part of application No. 08/840,765, filed on Apr. 16, 1997, now Pat. No. 6,482,585.

(51) Int. Cl.
*A01N 1/02* (2006.01)

(52) U.S. Cl. .......................................................... 435/2

(58) Field of Classification Search ....................... None
See application file for complete search history.

(56) References Cited

U.S. PATENT DOCUMENTS

| | | | |
|---|---|---|---|
| 5,747,536 A | 5/1998 | Cavazza | |
| 6,403,124 B1 * | 6/2002 | Dottori | ....................... 424/530 |
| 6,482,585 B2 | 11/2002 | Dottori | |
| 6,960,428 B2 | 11/2005 | Dottori | |

OTHER PUBLICATIONS

Sweeney, et al., "L-Carnitine and L-Acetylcarnitine May Reduce Glycolysis in Stored Platelet Concentrates", Vox Sanguinis, (Jun. 1998), 74, (1): 1226, 25th Congress of the International Society of Blood Transfusion, Oslo, Norway, Jun. 27-Jul. 2, 1998.

A. Arduini, et al., Addition of L-Carnitine to Additive Solution-Suspended Red Cells Stored at 4 Degrees Reduces In Vitro Hemolysis and Improves In Vivo Viability, Transfusion, Feb. 1997, 37 (2), pp. 166-174 (Abstract Only).

\* cited by examiner

*Primary Examiner*—Sandra Saucier
(74) *Attorney, Agent, or Firm*—Lucas & Mercanti, LLP

(57) ABSTRACT

Cell membrane maintenance of red blood cells and platelet concentrates is improved by the addition of 1 mM-10 mM L-carnitine and derivatives. This improvement allows extension of the period of viability of packed red blood cells and platelet concentrations beyond current periods. Additionally, the materials so treated exhibit extended circulation half life upon transfusion to a patient. Improvements in membrane maintenance achieved by this method permit irradiation of sealed containers of blood products so as to substantially sterilize and destroy leukocytes in the same.

5 Claims, 5 Drawing Sheets

METHOD OF REDUCING GLYCOLYSIS IN PLATELET CONCENTRATES USING L-CARNITINE, ALKANOYL CARNITINES AND SALTS THEREOF

This application is a divisional of U.S. patent application Ser. No. 10/756,368, filed on Jan. 14, 2004, which is continuation of U.S. patent application Ser. No. 10/055,900, filed on Jan. 28, 2002, which is a continuation of U.S. patent application Ser. No. 09/327,465, filed on Jun. 8, 1999, which is a continuation-in-part of U.S. patent application Ser. No. 08/840,765, filed on Apr. 16, 1997, which is incorporated herein by reference in its entirety.

BACKGROUND OF THE INVENTION

1. Field of the Invention

This invention pertains to a method of improving the storage stability, including resistance to hemolysis and improved viability, of blood products including packed red blood cells (RBCs), platelets and the like. Specifically, a method for extending the viability of these products, as well as their resistance to membrane damaging agents such as radiation, is provided by storing the products in a suspension including an effective amount of L-carnitine or an alkanoyl carnitine. The present invention also relates to a method for suppressing bacterial growth in whole blood and blood fractions, including packed red blood cells, packed white blood cells (WBCs), platelet concentrates, plasma, and plasma derivatives, which are stored for extended periods of time. The present invention further relates to a method and for reducing glycolysis in whole blood and blood fractions, including packed red blood cells, packed white blood cells (WBCs), platelet concentrates, plasma, and plasma derivatives, which are stored for extended periods of time.

2. Discussion of the Background

Concern has been steadily growing over both the national, and worldwide blood supplies. Both the integrity and reliability of existing supplies, and the ability to build larger stocks over time, have been brought into question. One reason for this is the relatively short period of storage stability of blood products. Currently, packed RBCs (red blood cell concentrates, or RCC), the dominant form of blood product for transfusions and the like, are limited to a 42-day storage period. After that time, ATP levels fall substantially, coupled with a significant loss of pH, strongly indicating a lack of viability, or, if viable, an extremely short circulation life upon infusion, in vivo. Whole blood is not stored for substantial periods. For platelets, the current storage period is even shorter, with the standard being 5 days at 22° C. The difference in storage stability of platelet concentrates (PC) has opposed to RBC, is due to ongoing metabolic reactions in platelets, due in part to the presence of mitochondria in PC, and their absence in RBCs. While both blood products show a drop in ATP, coupled with a drop in pH, over time, accompanied by the production of lactic acid, the presence of mitochondria in PC is likely to exacerbate the problem, due to glycolysis.

Simultaneously, concerns over the reliability and integrity of the blood supply have been raised. In particular, contamination of the blood supply with bacteria, or other microbiological agents, has been detected repeatedly. Such a situation is even more severe in countries with less sophisticated collection and storage methods. While agents may be added to collected products to reduce contamination, these are not desirable, given the need to transfuse the products back into recipient patients. One desirable alternative is radiation treatment of the products, after packaging, typically in plasticised vinyl plastic containers. Such radiation treatment would aggravate RBC and perhaps during PC storage, resulting in a diminished function of these cells.

Additionally, a small but growing portion of the blood receiving population is at risk of a generally fatal condition known as Transfusion associated graft versus host disease (TA-GVHD), which is due to the presence of viable allogenic leukocytes. This syndrome is typically associated with immunosuppressed patients, such as cancer and bone marrow transplant patients, but can also occur in immunocompetent persons in the setting of restricted HLA polymorphism in the population.

Substantial attention has been devoted to finding methods to extend storage stability. One such method, for extending the storage lifetime of PCs, is recited in U.S. Pat. No. 5,466,573. This patent is directed to providing PC preparations with acetate ion sources, which acts both as a substrate for oxidative phosphorylation and as a buffer to counteract any pH decrease due to lactic acid production. Such a method does not act directly on the problem of hemolysis, and membrane breakdown. An alternative method is disclosed in U.S. Pat. No. 5,496,821, by the inventor herein and commonly assigned. In this patent, whole blood is stored in a preparation including L-carnitine (LC) or alkanoyl derivatives thereof. The patent does not describe, however, the effects on blood products such as PC or RBC suspensions, and relies to at least some extent on the impact of LC on plasma characteristics.

As noted above, contamination of the blood supply with microbiological agents is another problem to be addressed by the medical community. One method of sterilizing the product, and improving reliability with respect to contamination, is to irradiate the blood product. In general, gamma irradiation values of about 25 centigray (cG), irradiating the product after it is sealed in a plastic, glass or other container is desirable. Regrettably, irradiation induces cell membrane lesions, with hemolysis in RBCs. Irradiation of blood products, including whole blood, packed RBCs and PCs continue to pose problems.

In addition, the effect of L-carnitine on bacterial growth in blood products, such as whole blood, red blood cell concentrates, and platelet concentrates, has not yet been reported. Similarly, the effect of L-Carnitine on glycolysis in blood products, such as whole blood, red blood cell concentrates, platelet concentrates, particularly prestorage-leuko-reduced random platelets, has not been demonstrated.

SUMMARY OF THE INVENTION

Accordingly, it is one object of those of skill in the art to provide a method to extend the period of viability, and the circulation half-life of RBCs and PCs upon transfusion, beyond the current maximums.

It is another object of those of skill in the art to find a way by which blood products, including whole blood, packed RBCs and PCs can be sterilized by irradiation, without substantial membrane damage and lesions, and hemolysis.

It is another object of the present invention to provide a method for suppressing bacterial growth in whole blood.

It is another object of the present invention to provide a method for suppressing bacterial growth in whole blood, which is stored for extended periods of time.

It is another object of the present invention to provide a method for suppressing bacterial growth in blood fractions.

It is another object of the present invention to provide a method for suppressing bacterial growth in blood fractions, which are stored for extended periods of time.

It is another object of the present invention to provide a method for suppressing bacterial growth in packed red blood cells.

It is another object of the present invention to provide a method for suppressing bacterial growth in packed red blood cells, which are stored for extended periods of time.

It is another object of the present invention to provide a method for suppressing bacterial growth in packed white blood cells.

It is another object of the present invention to provide a method for suppressing bacterial growth in packed white blood cells, which are stored for extended periods of time.

It is another object of the present invention to provide a method for suppressing bacterial growth in platelet concentrates.

It is another object of the present invention to provide a method for suppressing bacterial growth in platelet concentrates, which are stored for extended periods of time.

It is another object of the present invention to provide a method for suppressing bacterial growth in plasma or plasma derivatives.

It is another object of the present invention to provide a method for suppressing bacterial growth in plasma or plasma derivatives, which are stored for extended periods of time.

It is another object of the present invention to provide a method for reducing glycolysis in whole blood.

It is another object of the present invention to provide a method for reducing glycolysis in whole blood, which is stored for extended periods of time.

It is another object of the present invention to provide a method for reducing glycolysis in blood fractions.

It is another object of the present invention to provide a method for reducing glycolysis in blood fractions, which are stored for extended periods of time.

It is another object of the present invention to provide a method for reducing glycolysis in packed red blood cells.

It is another object of the present invention to provide a method for reducing glycolysis in packed red blood cells, which are stored for extended periods of time.

It is another object of the present invention to provide a method for reducing glycolysis in packed white blood cells.

It is another object of the present invention to provide a method for reducing glycolysis in packed white blood cells, which are stored for extended periods of time.

It is another object of the present invention to provide a method for reducing glycolysis in platelet concentrates.

It is another object of the present invention to provide a method for reducing glycolysis in platelet concentrates, which are stored for extended periods of time.

It is another object of the present invention to provide a method for reducing glycolysis in prestorage-leuko-reduced random platelets.

It is another object of the present invention to provide a method for reducing glycolysis in prestorage-leuko-reduced random platelets, which are stored for extended periods of time.

It is another object of the present invention to provide a method for reducing glycolysis in plasma or plasma derivatives.

It is another object of the present invention to provide a method for reducing glycolysis in plasma or plasma derivatives, which are stored for extended periods of time.

These and other objects, which will become apparent during the following detailed description, have been achieved by the inventor's discovery, through extended research, that the membrane damage experienced by RBCs and PCs upon storage, or in the face of irradiation, can be substantially delayed and suppressed, by suspending the blood product in a conventional preservation solution, such as AS-3, where the preservation solution further includes L-carnitine or an alkanoyl derivative thereof, in a concentration of 0.25-50 mM or more. Applicant's discovery lies in the recognition that most of the decomposition of blood products, conventionally associated with decreases in ATP levels, and pH, can be in fact traced to membrane damage and hemolysis. Membrane maintenance and repair may be effected by lipid reacylation, effected, in part, through LC, the irreversible uptake of which in RBC and similar blood products has been established through the inventive research. The inventor has also discovered that L-Carnitine suppresses bacterial growth in whole blood and blood fractions, including packed red blood cells, packed white blood cells (WBCs), platelet concentrates, plasma, and plasma derivatives, which are stored for extended periods of time. The inventor has further discovered that L-Carnitine reduces glycolysis in whole blood and blood fractions, including packed red blood cells, packed white blood cells (WBCs), platelet concentrates, particularly prestorage-leuko-reduced random platelets, plasma, and plasma derivatives, which are stored for extended periods of time.

DETAILED DESCRIPTION OF THE INVENTION

Figure 1:
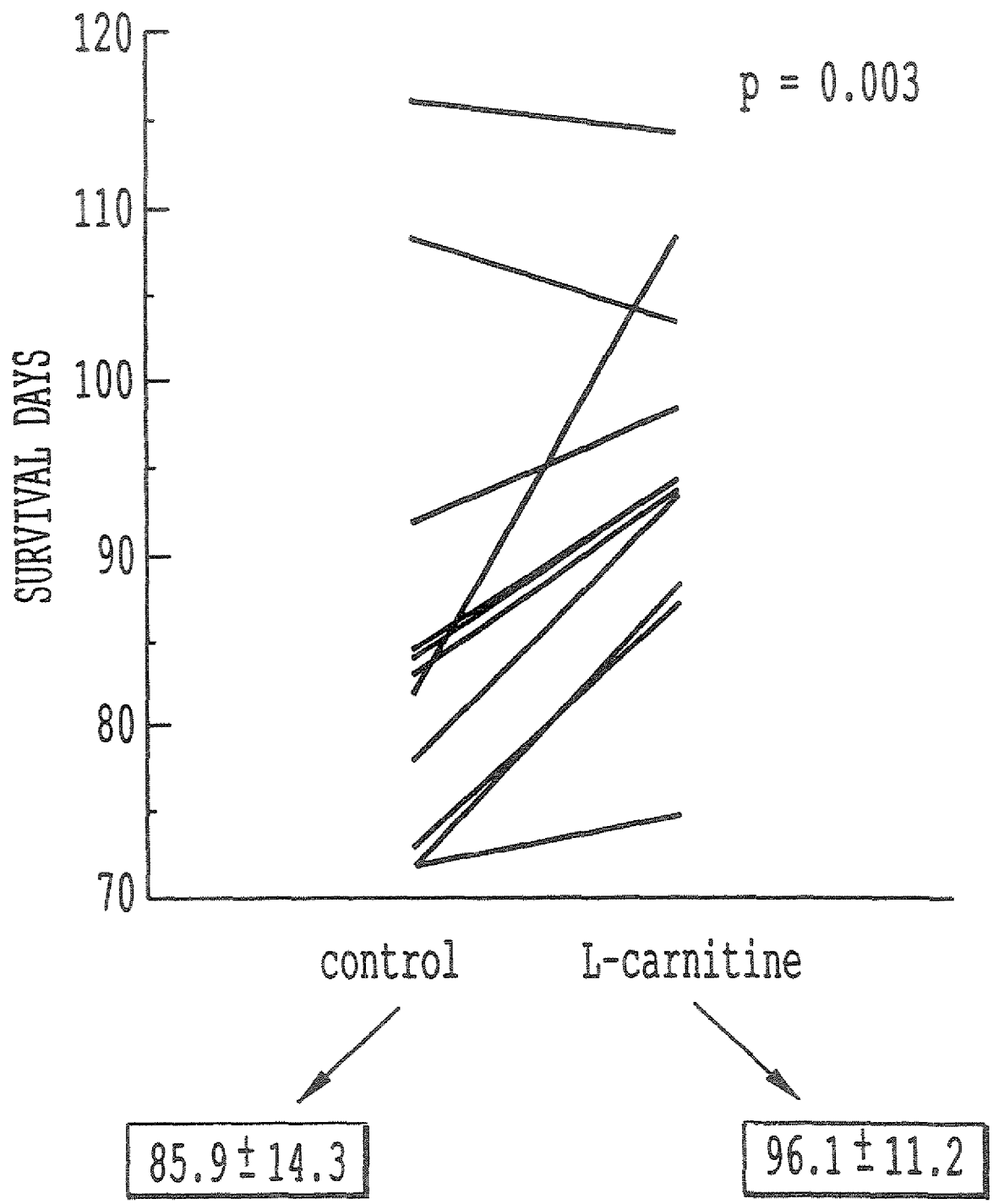
FIG. 1. Lifespan values after infusion of 42 days stored RBC as related to donor and to control and LC-stored. The arrows indicate mean±SD of control and LC-stored RBC, respectively. On top of the graph, the exact calculated p value is also shown.

This invention employs L-carnitine, and its alkanoyl derivatives, as an agent supporting cell membrane maintenance and repair, and suppression of hemolysis, in blood products. The present invention also provides a method for suppressing bacterial growth in whole blood and blood fractions, including packed red blood cells, packed white blood cells, platelet concentrates, plasma, and plasma derivatives. The present invention further provides a method for reducing glycolysis in whole blood and blood fractions, including packed red blood cells, packed white blood cells, platelet concentrates, plasma, and plasma derivatives.

Suitable alkanoyl L-carnitines include $C_{2-8}$-alkanoyl L-carnitines, and preferred alkanoyl L-carnitines include acetyl, butyryl, isobutyryl, valeryl, isovaleryl and particularly propionyl L-carnitine. Herein, reference is made to this family, generically, as LC, and exemplification is in terms of L-carnitine. The described alkanoyl L-carnitines, and their pharmalogically acceptable salts, however, may be used in place of L-carnitine.

Examples of suitable salts of L-carnitine include, e.g., L-carnitine chloride, L-carnitine bromide, L-carnitine orotate, L-carnitine acid aspartate, L-carnitine acid phosphate, L-carnitine fumarate, L-carnitine lactate, L-carnitine maleate, L-carnitine acid maleate, L-carnitine acid oxalate, L-carnitine acid sulfate, L-carnitine glucose phosphate, L-carnitine tartrate, L-carnitine acid tartrate, and L-carnitine mucate.

Examples of suitable salts of alkanoyl L-carnitine include, e.g., $C_{2-8}$-alkanoyl L-carnitine chlorides, $C_{2-8}$-alkanoyl L-carnitine bromides, $C_{2-8}$-alkanoyl L-carnitine orotates, $C_{2-8}$-alkanoyl L-carnitine acid aspartates, $C_{2-8}$-alkanoyl L-carnitine acid phosphates, $C_{2-8}$-alkanoyl L-carnitine fumarates, $C_{2-8}$-alkanoyl L-carnitine lactates, $C_{2-8}$-alkanoyl L-carnitine maleates, $C_{2-8}$-alkanoyl L-carnitine acid maleates, $C_{2-8}$-alkanoyl L-carnitine acid oxalates, $C_{2-8}$-alkanoyl L-carnitine acid sulfates, $C_{2-8}$-alkanoyl L-carnitine glucose phosphates, $C_{2-8}$-alkanoyl L-carnitine tartrates, $C_{2-8}$-alkanoyl L-carnitine acid tartrates, and $C_{2-8}$-alkanoyl L-carnitine mucates.

The addition of LC to whole blood or blood fractions, including RBCs, WBCs, PCs, plasma, and plasma derivatives requires LC to be present in an amount effective to permit membrane maintenance, repair and hemolysis suppression and/or to suppress bacterial growth and/or reduce glycolysis. The research undertaken, including the examples set forth below, has demonstrated a minimum effective range for the products of most donors of about 0.25 mM-0.5 mM. The upper limit is more practical than physiological. Concentrations as high as 50 mM or greater are easily tolerated. Values that are consistent with toxicological and osmological concerns are acceptable. Preferred ranges are 1-30 mM. A range of 1-10 mM or more is suitable with values between 4-6 mM making a marked difference. The effects of this invention, including the prolongation of viability, and the extension of circulation half-life upon transfusion, may be highly donor dependent. Accordingly, generally speaking, an effective concentration of LC is 0.5-50 mM, however, the ordinary artisan in the field may be required to extend that range, in either direction, depending on the particularities of the donor. Such extensions do not require inventive effort.

LC is consistent with conventional support solutions (stabilizing solutions), which are typically prepared to provide a buffering effect. Commonly employed solutions include ACED (citric acid-sodium citrate-dextrose), CPD (citrate-phosphate-dextrose) and modifications thereof, including CPD2/A-3, and related compositions. Typically, the composition includes a carbohydrate, such as glucose or mannitol, at least one phosphate salt, a citrate, and other balancing salts. LC is conventionally soluble and may be added to these compositions freely within the required range. Suitable solutions, are described in U.S. Pat. No. 5,496,821, incorporated herein-by-reference. Note, however, that support solutions other than those conventionally used, including artificial plasma and other physiologically acceptable solutions, can be used with LC in the invention. The important component of the support solution is LC.

The ability of LC, when included in whole blood or the suspension of blood fractions, such as RBCs, WBCs, PCs, plasma, and plasma derivatives to extend the viable time and therefore shelf length, and the circulation period upon transfusion into the receiving individual, is exemplified below by in vitro and in vivo experimentation. The experimentation employs LC, but alkanoyl L-carnitines can be employed. Of particular significance is the demonstration, below, that the improved performance is obtained through improved maintenance (including repair) of the cell membrane, and suppression of hemolysis.

Materials and Methods

Study Design I:

Evaluation of In Vivo and In Vitro Quality of RBC Stored with and without LC

Subjects. The subject population was male or female research subjects between the ages of 18 to 65 years with no known mental or physical disability and taking no drugs that might affect RBC viability. Individuals were recruited who fulfilled the conventional allogeneic donor criteria as listed in the Code of Federal Register, Chapter 2, the Standards of the American Association of Blood Banks, and the Blood Services Directives of the American National Red Cross. The study was approved by the Institutional Review Board of the Medical College of Hampton Roads and the subjects gave informed consent prior to participation in the study.

Each donor donated on two different occasions separated by 72 days, and was randomized to either the test or control arm on the first donation.

Blood storage system. Standard CP2D/AS-3 system (Miles, Inc.) Using polyvinyl chloride (PVC) plastic with diethyl-(n)hexyl-phthalate (DEHP) as plasticizer was used. For each test unit, 245 mg LC (in 1.1 mL pure, pyrogen-free solution in a sterilized glass bottle) was added to the container holding the AS-3 additive solution to give a final concentration of 5 mM. For the control units, 1.1 mL 0.9% NaCl was added to the AS-3 solution using the same conditions. Addition of LC or saline to the bags was performed by injecting through a sampling site coupler with a syringe. This was done in a laminar flow hood under UV light.

Donation & Processing. Standard phlebotomy and blood-drawing methods were used with collection of approximately 450±50 mL whole blood. The whole blood unit was held between 4-8 hours at room temperature before processing. The unit was centrifuged using standard conditions and, after centrifugation, the supernatant plasma was expressed off, and the sedimented packed RBC resuspended either in the standard AS-3 solution (control) or the carnitine-containing AS-3 solution (test). The suspended RBC units were stored at 4° C. for 42 days.

In Vitro Measurements: Measurements performed on pre-(0 day) and post-(42-day) samples included RBC ATP levels; total and supernatant hemoglobin; hematocrit (Hct); RBC, WBC, and platelet counts; RBC osmotic fragility; RBC morphology; lactate and glucose levels; supernatant potassium levels. These were performed using standard procedures as described previously, Heaton et al., Vox Sang 57:37-42 (1989).

In vivo Post-transfusion Measurements. After 42 days of storage, a sample was withdrawn and the stored cells labeled with Cr using standard methods. At the same time, to determine RBC mass, a fresh sample was collected from the donor for RBC labeling with 99 Tc. After labeling, 15 µCi $^{51}$Cr-labeled stored cells and 15 µCi $^{99}$Tc-labeled fresh cells were mixed and simultaneously infused. Blood samples (5 mL) were taken after the infusion at various time intervals for up to 35 days to calculate 24-hour % recovery and survival. The 24-hour % recovery was determined using either the single label method where log-linear regression of the radioactivity levels of samples taken at 5, 7.5, 10, and 15 min. was used to determine 0 time level, or by the double label method using donor RBC mass as determined by the $^{99}$Tc measurement.

Circulating lifespan of the transfused surviving Cr-labeled RBC was determined by samples taken at 24 hours and then twice weekly for up to 5 weeks. The radioactivity levels were corrected for a constant 1% elution per day. The data were fitted to a linear function with post-transfusion days as independent variable (x-axis) and the corrected Cr counts as dependent variable (y-axis). The lifespan of the RBC was then taken as the intersection of the fitted line with the x-axis.

Statistical analysis. Paired t-test or routine non-parametric statistical analysis was performed on data from the in vivo and in vitro testing of the units to determine if there were any statistically significant differences (1-tail) in the means between the test and control units. Statistical significance was considered at a p value less than 0.05.

Study Design II

Erythrocytes LC Uptake and Lipid Reacylation Studies with Storage Up to 42 Days

Chemicals. Essentially fatty acid-free bovine serum albumin (BSA) was obtained from SIGMA Chemical Company, St. Louis, Mo. (USA). [1-$^{14}$C]Palmitic acid (58 Ci/mol) was obtained from New England Nuclear Corporation, Boston, Mass. (USA). Thin-layer plates, Whatman LK6 (silica gel) (20×20 cm) with a pre-absorbent layer were obtained from Carlo Erba, Milan (Italy). Palmitoyl-L-carnitine (PLC) and LC were a kind gift of Sigma Tau, Pomezia (Italy). All other compounds used were reagent grade.

Red cell carnitine assay. Blood sample was withdrawn from the stored RCC unit and washed once with 4 vol. of cold 0.9% NaCl. RBC were then resuspended in 0.9% NaCl at a final hematocrit of 50%, and deproteinized with perchloric acid as described, Cooper et al., Biochem. Biophys. Acta 959: 100-105 (1988). Aliquots of the final extract were analyzed for free LC content according to the radiochemical assay of Pace et al., Clin. Chem. 24: 32-35 (1978).

Analysis of membrane complex lipid reacylation in stored RBC. Blood sample was withdrawn from stored RCC unit through a sampling site coupler with a syringe, and the sample processed immediately. This was done in a laminar flow hood under UV light. All the manipulations were conducted at 0-5° C. unless noted. RBC were washed two times with 4 vol. of cold 0.9% NaCl. Isolated RBC were once again washed with incubation buffer (NaCl 120 mM, KCl 5 mM, MgSO$_4$ 1 mM, NaH$_2$PO$_4$ 1 mM, saccharose 40 mM, 5 mM glucose, Tris-HCl 10 mM, at pH 7.4) and resuspended in the same buffer at a final hematocrit of 5%. A Rotabath shaking bath at 37° C. was used for the incubations. RBC were incubated with the radioactive palmitic acid (10 µM) complexed to fatty acid free BSA (1.65 mg/ml), Incubations were ended by washing cells once with cold incubation buffer, three times with fatty acid free BSA 1% in incubation buffer, and finally once again with incubation buffer. RBC lipids were extracted from intact cells with the Rose & Oaklander procedure, J. Lipid Res. 6: 428-431 (1965). In order to prevent lipid oxidation, 0.1% butylated hydroxytoluene was added to the lipid extracts. Aliquots of the lipid extract were used for determination of lipid phosphorus content, and analyzed by two dimensional thin layer chromatography. Briefly, the chromatograms were developed using chloroform-methanol-28% ammonia (65:25:5) in the first dimension. The chromatograms were then developed using chloroform-acetone-methanol-acetic acid-water (6:8:2:2:1) in the second dimension. Phosphatidylcholine (PC), a phosphatidylethanolamine (PE), and phosphatidylserine were visualized by brief exposure of the plates to iodine and identified using standards as a reference. Individual phospholipid spots were scraped off into vials containing scintillation fluid and radioactivity was determined by liquid scintillation counting. The identification and analysis of radioactive PLC was carried out as recently described, Arduini et al., J. Biol. Chem. 267: 12673-81 (1992). Counting efficiency was evaluated by an external standard. Calculations are based on the specific activities of radioactive palmitic acid.

Results

Study I

Pre-Storage AS-3 RCC Unit Characteristics

The properties of the AS-3 RCC products were as expected after the processing of the whole blood units. No significant difference between test and control units in the characteristics of the AS-3 RBC unit were observed as measured by unit volume, Hct, and WBC content, and in vitro RBC properties such as ATP levels, supernatant hemoglobin and potassium levels, osmotic fragility (Table I).

TABLE 1

RBC Pre-storage Characteristics of the Red Cell Concentrates

| | Control | Test (L-Carnitine) |
|---|---|---|
| Unit Volume (mL) | 305 ± 38 | 295 ± 41 |
| Unit Hct (%) | 60 ± 3 | 60 ± 3 |
| Unit WBC (×10$^9$) | 2.6 ± 1.1 | 2.4 ± 1.1 |
| ATP (µmol/g Hb) | 4.6 ± 0.2 | 4.3 ± 0.4 |
| Supernatant Hb (mg/dL) | 34 ± 15 | 26 ± 8 |
| Supernatant K+ (mEq/L) | 2.3 ± 0.2 | 2.2 ± 0.3 |
| Osmotic Fragility (%) | 50 ± 4 | 49 ± 4 |

Post-42 Day Storage RBC Characteristics

Metabolic. The amounts of glucose consumed and lactate produced during 42 days of storage were similar for test and control units (Table 2). As expected, an inverse high correlation was found between these two parameters of glycolysis (r=0.76). However, less hemolysis and higher ATP levels were found for carnitine-stored RBC units as compared to control. As illustrated in FIG. 1 this higher ATP level was observed in all but one pair (p<0.01).

TABLE 2

Post-Storage (42 days) Characteristics of the Red Cell Concentrates

|  | Control | Test (L-Carnitine) |
|---|---|---|
| In Vitro parameters |  |  |
| Glucose (mg/dL) | 208 ± 33 | 193 ± 40 |
| Lactate (mg/dL) | 201 ± 27 | 199 ± 37 |
| pH | 6.33 ± 0.03 | 6.32 ± 0.04 |
| ATP (μmol/g Hb) | 3.01 ± 0.42 | 3.24 ± 0.38* |
| Hemolysis (%) | 0.47 ± 0.41 | 0.30 ± 0.22* |
| Supernatant K+ (mEq/L) | 61 ± 4 | 60 ± 3 |
| Osmotic Fragility (%) | 51 ± 3 | 50 ± 4 |
| Morphological Score | 69 ± 8 | 68 ± 15 |
| In Vivo parameters |  |  |
| 24 Hr % Recovery (single label) | 81.1 ± 6.2 | 84.0 ± 4.4 |
| 24 Hr Recovery (double label) | 80.1 ± 6.0 | 83.9 ± 5.0* |
| RBC Mass (mL) | 1634 ± 510 | 1591 ± 534 |
| Survival (days) | 85.9 ± 14.3 | 96.1 ± 11.2* |

*($p < 0.05$)

Figure 2:
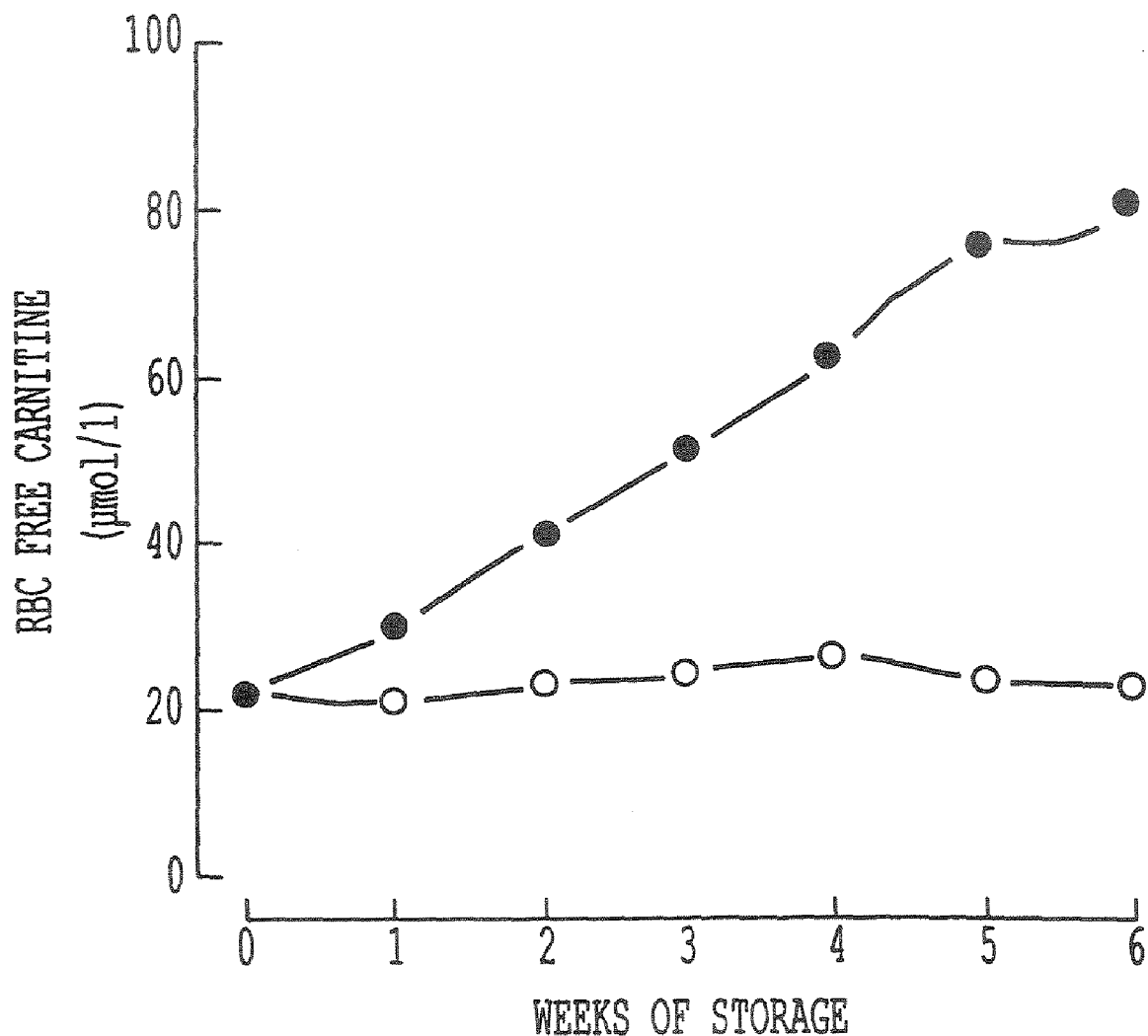
FIG. 2. Red cell carnitine content at different weeks of blood preservation. Carnitine was assayed as described in Materials and Methods. Values are the average of three experiments done in duplicate. The variation between experiments was not more than 7%. Open symbols, RBC stored with AS-3 alone; closed symbols, RBC stored in AS-3 supplemented with LC (5 mM).

Membrane. Percent hemolysis at the end of storage levels was less with the carnitine units, as shown in FIG. 2. On the other hand, no significant differences were found with regard to supernatant potassium levels, osmotic shock response, and morphology score which were within expected range at the end of 42 days of storage.

Post transfusion viability. The mean 24-hour % recovery for the control units was similar to what previously has been found by us and by others. However, mean % recoveries for the carnitine-stored red cells were higher than the control-stored cells ($p<0.05$). In addition, the mean circulating lifespan of the infused stored red cells was also higher for the carnitine-stored cells (FIG. 1). The donors' RBC mass as determined on the two occasions were highly similar ($r=0.98$) and statistically not different.

Correlation studies. As expected, 24-hour % recovery showed significant correlations with ATP levels ($r=0.63$) and other measurements of RBC membrane integrity such as hemolysis ($r=0.57$), osmotic fragility ($r=0.71$), and morphology score ($r=0.59$). Percent hemolysis correlated highly with ATP levels ($r=0.83$) and also with the WBC content of the RBC units ($r=0.83$). The RBC circulating lifespan showed no significant correlations with any in vitro parameter.

Study II

Carnitine Uptake in Stored RBC

RBC stored in AS-3 medium alone did not show any significant loss of the LC content throughout the storage (FIG. 2). This is in agreement with findings by Cooper et al., supra showing that human red cell LC does not freely exchange with either plasma or isoosmotic buffer. When red cells were stored in AS-3 supplemented with LC, higher amounts of intracellular LC than AS-3 alone were detected (FIG. 2). LC content increased linearly during times of storage, reaching a 4 fold increase at 42 days.

Membrane Complex Lipid Reacylation Studies in Stored RBC

Figure 3:
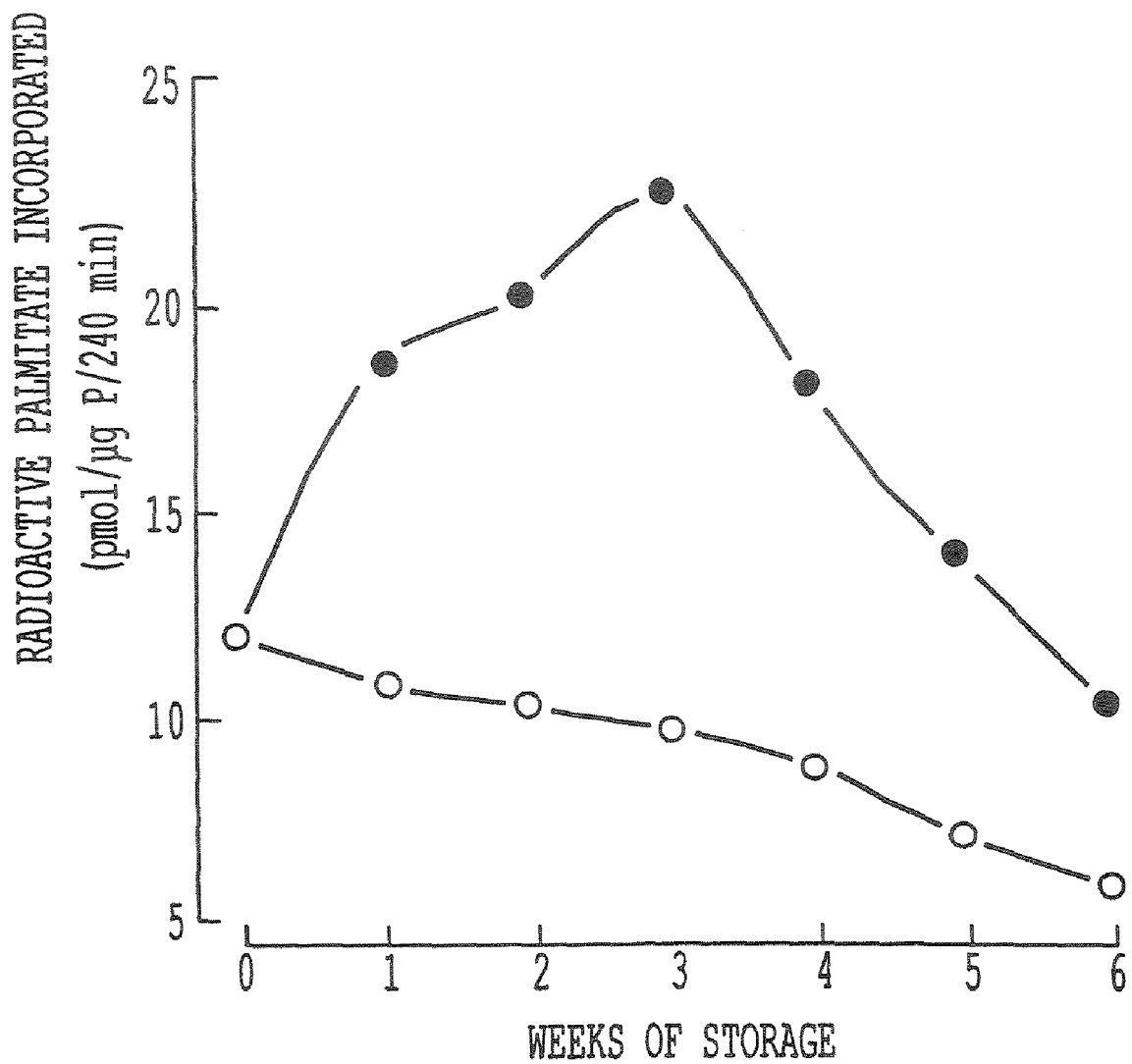
FIG. 3. Radioactive palmitic acid incorporation into RBC LC at different weeks of blood preservation. RBC aliquots withdrawn either from blood unit stored in AS-3 alone or AS-3 plus LC were incubated at 37° C. with [1-$^{14}$C]palmitic acid complexed to fatty acid free BSA. At the end of incubation, RBC were then processed as described in Materials and Methods. Radiolabeled PLC formation was referred to the phosphorous content present in lipid extract. Values are the average of three experiments done in duplicate. The variation between experiment was not more than 7%. Open symbols, RBC stored with AS-3 alone; closed symbols, RBC stored in AS-3 supplemented with LC (5 mM).
Figure 4A:
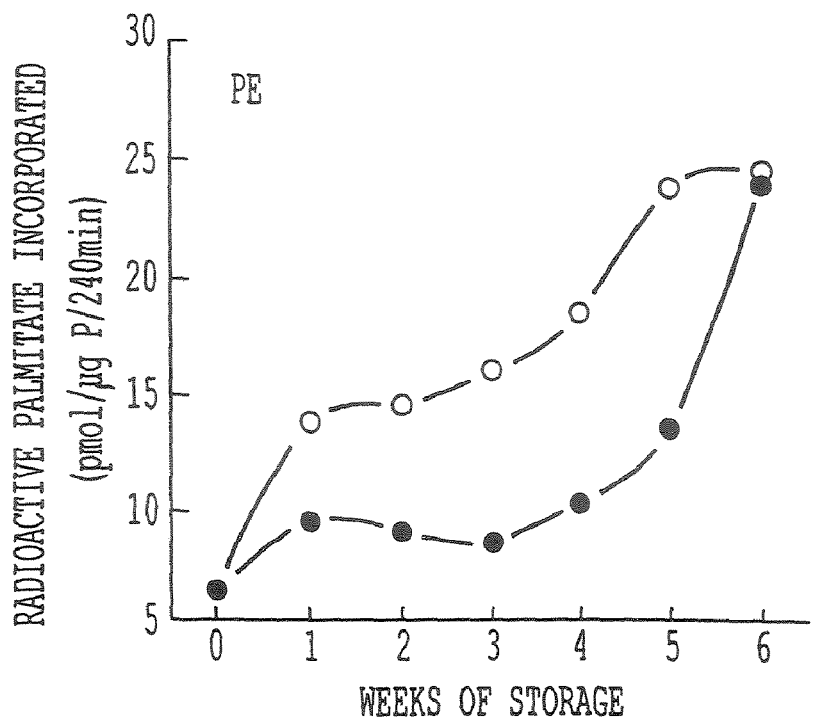
FIG. 4. Radioactive palmitic acid incorporation into red cell membrane of phosphatidylethanolamine (PE) and phosphatidylcholine (PC) at different weeks of blood preservation. RBC aliquots withdrawn either from blood unit stored in AS-3 alone or AS-3 plus LC were incubated at 37° C. with [1-$^{14}$C]palmitic acid complexed to fatty acid free BSA. At the end of incubation, RBC were then processed as described. Results are given as pmol [1-$^{14}$C]palmitic acid/µg lipid phosphorous present in lipid extract. Values are the average of three experiments done in duplicate. The variation between experiments was not more than 7%. Open symbols, RBC stored with AS-3 alone, closed symbols, RBC stored in AS-3 supplemented with LC (5 mM).
Figure 4B:
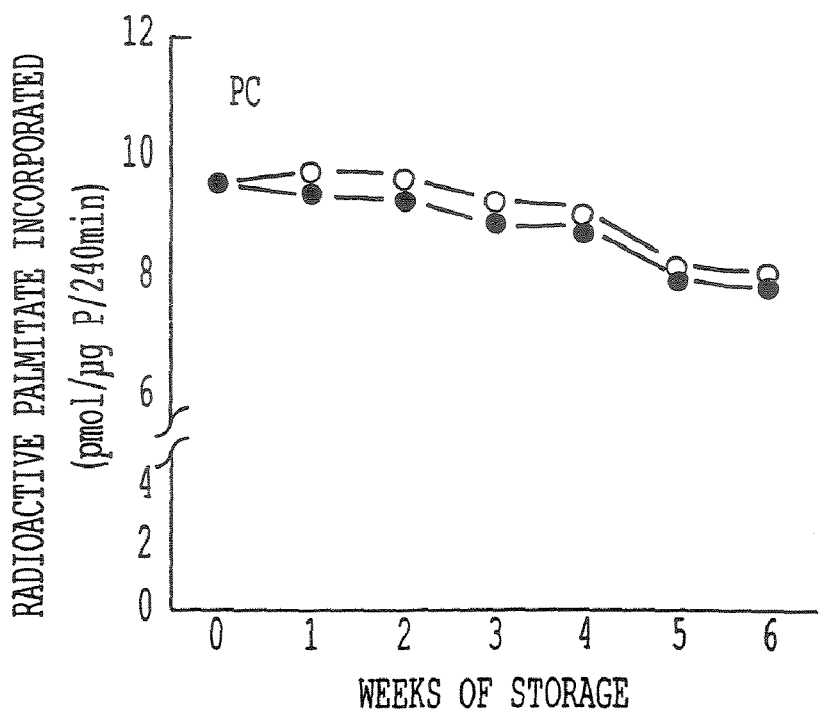

With no carnitine present the radioactive palmitate incorporated into PLC decreased linearly with the time of storage (FIG. 3). At variance, red cell from RCC unit stored in the LC-containing the AS-3 solution showed an initial increase (with a nadir at the 3 week) followed by a rapid decrease of the radioactive palmitate incorporated into PLC. In the same red cell preparations, the incorporation of radioactive palmitate into membrane phospholipids was also evaluated. Radioactive palmitate incorporation into membrane PE of red cells from blood unit stored in the AS-3 solution alone showed a constant significant increase of radioactivity into PE throughout the storage period (FIG. 4). Red cells stored in the presence of LC were characterized by a sudden increase of PE reacylation toward the end of the storage, with a nadir at the 6$^{th}$ week (FIG. 4). Radioactive palmitate incorporation rates into membrane PC decreased slightly throughout the storage, and no differences were observed between the two red cell preparations (FIG. 4). It should be pointed out that since in our reacylation studies red cells were incubated at 37° C. in a Krebs Ringer buffer containing glucose, ATP levels at the end of the incubation were close to physiological values (data not shown).

Discussion

In this study, in vitro and in vivo testing of RBC units at the end of 42 days of storage demonstrated significant differences between carnitine-stored RBC as compared to control-stored RBC. Various in vitro RBC properties reflective of metabolic and membrane integrity such as ATP and % hemolysis, as well as direct measure of cell viability (24-hour % recovery and circulating lifespan) were significantly superior for carnitine-stored RBC. A prolongation of the mean lifespan of the surviving RBC circulating at 24-hours after infusion is of interest. This finding may be related to the irreversible uptake of LC during storage, an unprecedented and unexpected discovery. The values obtained in the control studies for various RBC properties were as expected and not different from previous studies. At the time of blood collection, no significant differences in unit or RBC characteristics between test and control were found. As illustrated in FIGS. 1-3, RBC ATP levels, % hemolysis, and circulating lifespan were strongly donor-related, and, since the study was a randomly paired design with five test and five control studies performed on both the first and second occasions, it is unlikely that the observed differences could be due to chance or to any faulty study design. It is, therefore, most likely that the observed differences found in this study were caused by the addition of carnitine to the test units. The possibility that the increased lifespan reflects decreased elution of Cr cannot be excluded, but is not consistent with the improved in vitro measures of the stored red cells that has been found to correlate with in vivo viability.

Several investigations have found that LC and its acyl-esters have a cytoprotective/membrane stabilizing effect on various cells including red cells. See, e.g., Snyder et al., Arch. Biochem. Biophys. 276: 132-138 (1990). In this study it was found that LC was irreversibly taken up by the RBC during storage. Although the nature of this process is not entirely clear, one would exclude the participation of a specific carrier for the LC uptake. To our knowledge, the only known LC carrier operates in cellular systems where the intracellular concentration of LC is several fold higher than that normally present in the extracellular environment. Red cell LC concentration is similar to that of the plasma. Thus, irrespective of the low temperature, APT depletion, and other possible metabolic changes occurring during the storage, when red cells are stored in a medium containing relatively high amounts of exogenous LC, a unidirectional uptake of LC by the cells seems to be established. Nothing in the art appears to predict this.

The nature of the action of LC on stored RBC could be viewed either as a biophysical and/or metabolic intervention on the membrane compartment. Post-transfusion survival of stored red cells is related to the integrity of membrane function as suggested by the significant correlation between the in vivo viability of reinfused red cell and its surface-to-volume ratio measures. A major contributor to RBC membrane structure and function is represented by the cytoskeleton network, Marchesi, Ann. Rev. Cell Biol. 1: 531-536 (1985), a supramolecular protein organization lying beneath the inner hernileaflet of RBC membrane. Wolfe et al in a survey study on the composition and function of cytoskeletal membrane protein of stored red cells found that the only relevant change was a decreased capability of spectrin to associate with actin either in the presence or absence of protein 4.1. Wolfe et al., J. Clin. Invest. 78: 1681-1686 (1986). We have shown that LC affect RBC membrane deformability of protein 4.1 containing resealed ghosts subjected to increased shear stress. Arduini et al., Life Sci. 47: 2395-2400 (1990). Thus, LC may exert a stabilizing effect of the membrane through a spectrin interaction with one or more cytoskeletal components. A recent electron paramagnetic resonance study of Butterfield and Rangachari, Life Sci. 52:297-303 (1992), on the red cell spectrin-actin interaction showed that LC significantly reduced the segmental motion of spin-labeled sties on spectrin, confirming the previous suggestion of an involvement of LC in strengthening the interaction between spectrin and actin, Arduini et al., supra.

In addition to a potential biophysical action described above, the improvements observed in the LC-stored red cells may also be the result of a favorable metabolic process. Normally, the deacylation-reacylation cycle of membrane phospholipids requires ATP for generation of acyl-CoA. The acyl moiety of acyl-CoA is then transferred into lysophospholipids by lysophospholipid acyl-CoA transferase. In addition, during an oxidative challenge, the membrane repair process of RBC phospholipids follows the same metabolic pathway. Recent findings have shown that CPT affect the reacylation process of membrane phospholipids in red cells and neuronal cells by modulating the size of the acyl-CoA pool between the activation step of the fatty acid and its transfer into lysophospholipids. Arduini et al., J. Biol. Chem. 267: 12673-12681 (1992). In addition, pulse-chase and ATP depletion studies have demonstrated that the red cell acylcarnitine pool serves as a reservoir of activated acyl groups at no cost of ATP. Arduini et al., Biochem. Biophys. Res. Comm. 187: 353-358 (1994).

The enhancement of radioactive palmitate incorporation into membrane PE of red cells stored in AS-3 alone suggests that long term storage (with a progressive RBC ATP depletion) causes an increased demand of activated acyl units for the reacylation of membrane phospholipids (FIG. 4). During the first five weeks of storage, red cells preserved in AS-3 without LC seem to incorporate more palmitate into PE than red cells stored in AS-3 containing LC (FIG. 4). Red cells stored in the presence of LC were able to incorporate more palmitate into PE at the end of the storage. This finding may suggest that an oxidative challenge is somehow operative, since the exposure of red cells to oxidant strongly stimulates the membrane PE reacylation process, but not that of membrane PC. Dise et al., Biochem. Biophys. Acta 859: 69-78 (1986). Of interest, during the first five weeks of storage, red cells preserved in AS-3 alone seem to incorporate more palmitate into PE than red cells stored in AS-3 containing LC (FIG. 4). This suggests that in the latter case CPT may compete with the reacylating enzyme for acyl-CoA utilization. In agreement with this concept, however, we should have observed a much greater difference at the end of the storage period, when the acyl-CoA requirement for the reacylation process is the highest, This was not the case. Red cells stored with or without LC showed a similar incorporation rate at the end of the storage (FIG. 4). In addition, we have shown that red cell CPT, under a variety of different experimental conditions, does not compete with the reacylation of membrane phospholipids. Arudini et al., Life Chem. Rep. 12: 49-54 (1994).

Figure 5A:
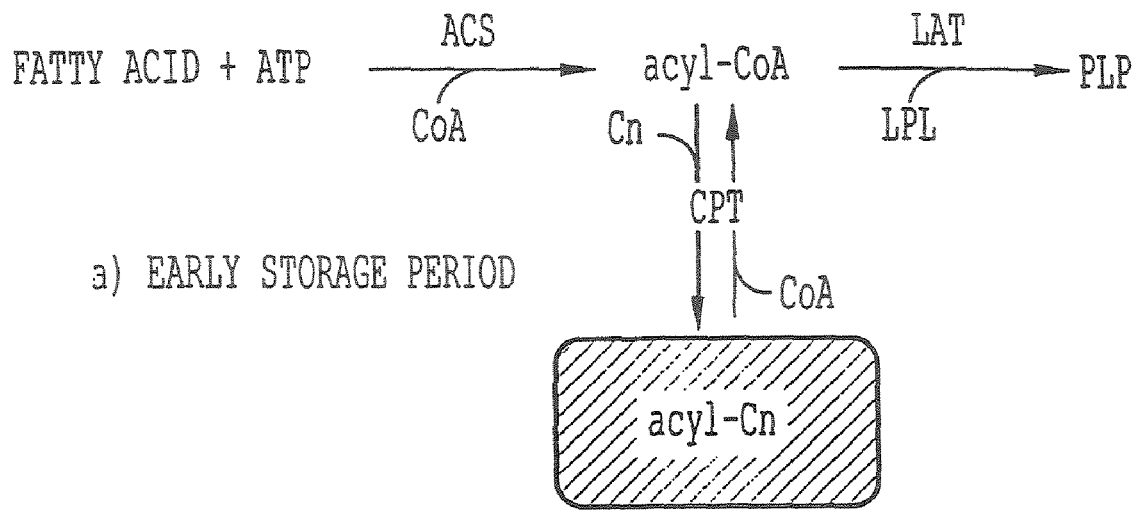
FIG. 5. The carnitine system and membrane phospholipid reacylation reactions. Thicker arrows indicate the preferential acyl flux. The dimension of the acylcarnitine box shows the likely related pool size. Abbreviations used are: LPL, lysophospholipids; PLP, phospholipids; Cn, carnitine; acyl-Cn, acyl-carnitine; ACS, acyl-CoA synthetase; LAT, lysophospholipid acyl-CoA transferase; CPT, carnitine palmitoyltransferase.
Figure 5B:
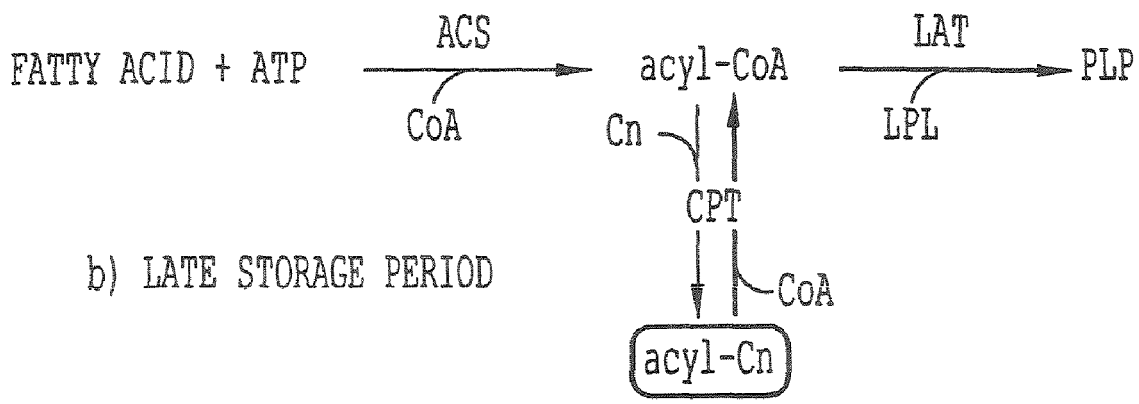

Radioactive PLC formation in the LC-supplemented red cells is greater than that found in red cells stored without LC (FIG. 3). In addition, the time course of PLC formation in red cells stored with LC showed an interesting bell shape cue with a nadir at the third week of storage. The radioactive PLC formation is reflective of the pool size of cold long-chain acylcarnitine and the direction of CPT-mediated acyl flux in intact red cells. During the first three weeks of storage with relatively high glycolytic activity and APT availability, CPT seems to drive the acyl flux toward acylcarnitine in red cells stored in the presence of LC (FIG. 5a). After the third week of storage, with LC present the flux is then reversed. These changes may reflect essentially the ability of CPT to buffer activated acyl-units: an increased requirement of acyl-CoA for the reacylation process results in a lower production of PLC and vice versa, and may represent a mechanism where CPT is used to buffer the increase of demand of acyl units for the reacylation process (FIG. 5b).

The higher 24-hour % recovery and circulating lifespan represents an improvement of approximately 15% in terms of potency (amount of transfused circulating RBC available to the recipient times average lifespan). This increase in potency could translate clinically into a reduction in transfusion requirements in chronically transfused patients such as in thalassemics or in patients with bone marrow failure. Alternatively, it may be possible to extend the shelf-life of liquid stored RBCs.

Our findings suggest that the presence of LC in the preservation medium during RBC storage may have a sparing action on the ATP pool used by the reacylation of phospholipids for membrane repair. This favorable metabolic process, associated with a possible beneficial biophysical action, may thus explain the reduced hemolysis, higher ATP levels, and the improved in vivo recovery and survival of the LC-stored red cells.

Irradiation

The problem of contamination of blood products, including whole blood, RBC, RCC, PC and the like, can be reduced by substantial amount by irradiation. Levels of irradiation necessary for sterilization, and substantially 100% mortality of microbiological agents, have been widely explored. Additionally, more importantly, leukocytes may be destroyed by similar irradiation. A variety of types of irradiation can be used, including gamma radiation (Cobalt GG, Van de Graf acceleration), UV irradiation, infrared irradiation, etc. A close equivalent to about 20-50 cG gamma irradiation is sufficient.

Worldwide, between 60 and 80 million units of whole blood are collected annually and used in the transfusion support of a variety of patient populations. In the underdeveloped countries collection rates per 1000 population are lower and most blood transfusions are given in the treatment of obstetrical and pediatric cases, particularly malaria associated anemia. In the developed countries, collection rates per 1000 population are 50-10 times higher and most transfusions are given in surgery (50%) or in the treatment of patients with cancer associated anemia, bone marrow transplantation, non-malignant gastrointestinal bleeding (FIG. 1). There are many potential adverse effects associated with the transfusion of allogenic blood. One particular complication adversely associated with blood transfusion is the rare and usually fatal entity known as Transfusion associated graft versus host disease (TA-GVHD), a complication mediated by viable allogenic immunocytes.

TA-GVHD disease is a rare complication of blood transfusion potentially seen in two types of blood transfusion recipient patient populations. TA-GVHD has a mortality approaching 100% and prevention is the only effective approach at this time. First, in immunocompromised patients, such as patients after bone marrow or other organ transplantation, Hodgkins disease or hereditary deficiencies of the immune system. Second, in nonimmunocompromised patients, when HLA similarity exists between blood donor and blood recipient. This is most often seen in directed donations from close relatives or in populations of more limited HLA polymorphism such as in Japan and Israel. On account of this, it is universal practice to irradiate cellular blood products with gamma irradiation to a mid-plane dose of approximately 25 centigray (cG) in order to destroy the replicating ability of viable immunocytes. It should be noted that TA-GVHD is associated with cellular products which are fresh, i.e. generally less than 15 days. However, "aging" of blood is not as yet an accepted practice in preventing this complication. Although the immunocytes are part of the allogenic leukocyte population, the degree of leukodepletion currently achieved with third generation filters is not considered currently adequate to prevent this complication. Thus, gamma radiation at this time remains the only accepted prophylactic intervention.

The difficulty with gamma irradiation of red cells in particular is the potential to damage the cell membrane. It is clear that irradiation at this dose produces a loss in potency of approximately 7-8% as measured in vitro by a reduction in red cell ATP, increased hemolysis, and increased supernatant potassium. These changes are consistent with a membrane damage effect. These in vitro changes are associated with a reduction in the 24 hour recovery of gamma irradiation red blood cells. With regard to platelet products, at least one publication has suggested some loss in viability.

Considerable evidence indicates that gamma irradiation exerts its effects by generating activated oxygen species, such as singlet oxygen, hydroxy, radical, and superoxide anion. These species induce intracellular damage to DNA and, thus, prevent cell replication, a prerequisite to TA-GVHD. However, these same oxygen species may oxidize membrane lipids on the red cell and possibly platelet membrane, inducing a membrane lesion which reduces the quality (potency) of the cellular product.

LC is known to play a key role in the transportation of long chain fatty acids across the mitochondrial membrane. Hereditary disorders in which there is a failure of the carnitine system to transport long chain fatty acids results in significant impairment in skeletal muscle function. Recently, there has been increasing interest in the role of LC in red cell membrane. What has been surprising, however, is that red cells lack mitochondria, and thus, considerable curiosity surrounding the presence of LC and carnitine palmitoyl transferase, an enzyme involved in reversible acylation of LC. It was at first unclear as to the role which these might play within red cells. The red cell may be subjected to oxidant stress throughout it's long life cycle in vivo, and repair of oxidized membrane lipids involving LC could be important for the normal survival of red cells.

Early increase in acylated carnitine during a time of increased ATP availability may function as a reservoir of activated fatty acids, which can subsequently be used in a repair mechanism for damaged oxidized membranes lipids. Such an explanation would well explain the reduced hemolysis observed during the in vitro storage of red blood cells supra and in addition, would explain the improvement observed with in vivo recovery and survival. The net effect of LC addition is an approximate 17% increase in potency.

Accordingly, LC may be used to abrogate or prevent membrane lesions induced by irradiation. This would occur through the ability of carnitine stored in red cells to repair oxidized membrane lipids in vitro.

To limit blood products' (RCC, PC and the like) susceptibility to membrane lesions and hemolysis, the blood product may be first suspended in a solution including LC in an amount of 0.25 mM-50 mM, cell membrane maintenance and suppression of hemolysis is achieved to a sufficient degree that the sealed product can be irradiated for the purposes of sterilization, and subsequently may enjoy an extended shelf life and circulation half-life after transfusion. Viability on the order of current viabilities can be achieved, with materials more nearly certain to be sterile and unlikely to introduce TA-GVHD, due to irradiation after sealing the blood product suspension. It it to be emphasized that the term blood product, in this connection, is to be interpreted broadly, to include whole blood, blood plasma, RCCs, PCs, mixtures and the like.

I. The Use of L-Carnitine to Suppress Bacterial Growth in Extended-Storage Platelet Concentrates.

Background: L-Carnitine (LC) reduces glycosis in extended (>5 days) stored platelet concentrates (Sweeny et al, $25^{th}$ Congress of the International Society of Blood Transfusion. Oslo, Norway, Jun. 27-Jul. 2, 1998, in Vox Sanguinis, vol. 74, No. Suppl. 1, p. 1226; and Sweeny et al, The American Society of Hematology, $40^{th}$ Annual Meeting, Miami Beach, Fla., USA, Dec. 4-8, 1998). The effect of LC on bacterial growth in platelet concentrates is important to evaluate if LC is to be used as an additive.

Study Methods: Two ABO identical prestorage-leuko-reduced platelet concentrates produced by in line filtration of platelet rich plasma (MedSep Corp. Covina, Calif.) were pooled, then equally divided into two CLX® (MedSep) bags. Either LC, to a final concentration of 5 mM, or saline (control) was added to one of each pair. Each container was spiked with 1 ml of a coagulase negative staphylococcal suspension on Day 0 to a final concentration between 1-48 CFU/mL. Samples were removed from each container aseptically on Day 3, Day 6 and either Day 7 or Day 8 for colony count. Data were analyzed by paired t tests.

Results: Eleven pairs of concentrates were studied. The results obtained are shown in the Table below. By Day 7/8, growth in the L-Carnitine containers was 33% that of controls.

Conclusion: L-Carnitine at 5 mM retards the growth of coagulase negative staphylococci in liquid stored platelet concentrates.

|         | Pair | Control*      | L-Carnitine*  | p     |
|---------|------|---------------|---------------|-------|
| Day 0   | 11   | 1.12 ± 0.7    | 1.12 ± 0.7    | N/A   |
| Day 3   | 11   | 3.11 ± 0.7    | 3.04 ± 0.7    | 0.43  |
| Day 6   | 8    | 4.28 ± 1.3    | 3.88 ± 1.0    | 0.05  |
| Day 7/8 | 11   | 5.09 ± 1.5    | 4.60 ± 1.5    | 0.002 |

*Bacterial growth expressed in Log CFU/ml

II. The Use of L-Carnitine to Reduce Glycolysis During the Extended Storage of Prestorage-Leuko-Reduced Random Platelets.

Background: L-Carnitine reduces glycolysis in standard (non-leuko-reduced) platelet concentrates stored for five-ten days (Sweeny et al, 25th Congress of the International Society of Blood Transfusion. Oslo, Norway, Jun. 27-Jul. 2, 1998, in *Vox Sanguinis*, vol. 74, No. Suppl. 1, p. 1226; and Sweeny et al, The American Society of Hematology, 40th Annual Meeting, Miami Beach, Fla., USA, Dec. 4-8, 1998). A similar effect on prestorage-leuko-reduced random donor platelets has not been previously demonstrated.

Study Deign: Two ABO identical prestorage-leuko-reduced platelet concentrates produced by in-line filtration of platelet rich plasma (MedSep Inc., Corvina, Calif.) were pooled, then equally divided into two CLX (MedSep) containers. Either L-Carnitine (final concentration 5 mM) or saline was added to one bag of each pair of platelets. Platelets were stored for either seven or eight days at 22° C. on a flatbed agitator, then tested. Tests performed were pH, platelet count, supernatant glucose and lactate, surface p-selectin expression by flow cytometry, extent of shape change (ESC) and hypotonic shock response (HSR). Glucose consumption and lactate production were calculated as $mM/10^{12}$ platelets/day. Data were analyzed using paired t-tests.

Results: Seven (7) pairs of platelet concentrates were studied. The results obtained are shown in the Table below.

Conclusion: L-Carnitine reduces glycolysis in stored prestorage-leuko-reduced random donor platelets.

|  | Control | L-Carnitine | p |
| --- | --- | --- | --- |
| pH | 6.97 ± 0.2 | 7.09 ± 0.1 | <0.01 |
| Glucose concentration | 1.25 ± 0.2 | 1.13 ± 0.2 | <0.01 |
| Lactate production | 1.73 ± 0.3 | 1.50 ± 0.2 | <0.01 |
| P-selectin (% positive) | 74 ± 4 | 69 ± 9 | 0.04 |
| ESC (%) | 11 ± 5 | 12 ± 4 | 0.35 |
| HSR (%) | 45 ± 13 | 50 ± 22 | 0.64 |

The invention of this patent application has been disclosed in both generic terms and by reference to specific examples. Variations will occur to those of ordinary skill in the art without the exercise of inventive faculty. In particular, alternate stabilizing compositions, blood products, preservatives, inhibitors and the like may be modified, without the exercise of inventive skill. Additionally, specific levels, viability periods and circulation half-lifes will vary from donor to donor, and recipient to recipient. Such variations remain within the scope of the invention, unless specifically excluded by the recitations of the claims set forth below.

The invention claimed is:

1. A method of reducing glycolysis in a blood fraction, comprising adding to a blood fraction a compound selected from the group consisting of L-carnitine, salts of L-carnitine, alkanoyl carnitines, salts of alkanoyl carnitines, and mixtures thereof, in an amount effective to reduce glycolysis in said blood fraction,
   wherein said blood fraction is a platelet concentrate, and wherein said method comprises suspending said platelet concentrate in a support solution which comprises said compound.

2. The method of claim 1, wherein said compound is comprised in a support solution in a concentration of 0.25 to 50 mM.

3. The method of claim 1, wherein said compound is comprised in a support solution in a concentration of 1 to 30 mM.

4. The method of claim 1, wherein said compound is L-carnitine.

5. The method of claim 1, wherein said compound is selected from the group consisting of acetyl L-carnitine, propionyl L-carnitine, butyryl L-carnitine, isobutyryl L-carnitine, valeryl L-carnitine, and isovaleryl L-carnitine.

* * * * *